US012276586B2

(12) United States Patent
Laor

(10) Patent No.: US 12,276,586 B2
(45) Date of Patent: Apr. 15, 2025

(54) METHOD AND SYSTEM FOR DETECTING NON-VOLATILE AND SEMI-VOLATILE ORGANIC COMPOUNDS IN MID-IR SPECTROMETRY GAS CELL CONFIGURATIONS

(71) Applicant: BREATH OF HEALTH LTD., Rehovot (IL)

(72) Inventor: Marsel Arie Laor, Zichron-Yaacov (IL)

(73) Assignee: BREATH OF HEALTH LTD., Rehovot (IL)

( * ) Notice: Subject to any disclaimer, the term of this patent is extended or adjusted under 35 U.S.C. 154(b) by 318 days.

(21) Appl. No.: 18/072,613

(22) Filed: Nov. 30, 2022

(65) Prior Publication Data

US 2024/0175791 A1 May 30, 2024

(51) Int. Cl.

| | |
|---|---|
| ***G01N 1/38*** | (2006.01) |
| ***G01N 1/42*** | (2006.01) |
| ***G01N 1/44*** | (2006.01) |
| ***G01N 21/35*** | (2014.01) |
| ***G01N 21/3504*** | (2014.01) |
| ***G01N 33/497*** | (2006.01) |

(52) U.S. Cl.

CPC ................. *G01N 1/38* (2013.01); *G01N 1/42* (2013.01); *G01N 1/44* (2013.01); *G01N 21/3504* (2013.01); *G01N 33/497* (2013.01); *G01N 2021/3595* (2013.01)

(58) Field of Classification Search

CPC .. G01N 1/38; G01N 1/42; G01N 1/44; G01N 21/3504; G01N 33/497; G01N 2021/3595; G01N 33/56983; G01N 33/6848; A61B 5/0075; A61B 5/14546; A61B 5/7246; A61B 5/082; A61B 5/097

USPC ............................................................ 356/36

See application file for complete search history.

(56) References Cited

U.S. PATENT DOCUMENTS 7,972,277 B2 * 7/2011 Oki ...................... G01N 33/497 600/529
8,316,852 B2 * 11/2012 Pouteau .................... B03C 3/49 95/79

* cited by examiner

*Primary Examiner* — Seung C Sohn
(74) *Attorney, Agent, or Firm* — Pillsbury Winthrop Shaw Pittman, LLP

(57) ABSTRACT

The embodiments provide a system including a pump configured to pump an air sample, from a container to a cooling chamber, the cooling chamber configured to cool the exhaled air sample to a sub-zero temperature, and is in fluid communication with an injector unit. The injector unit mixes the cooled air sample and inert gas and injects the mixed air sample at a high velocity to a test chamber. Further provided is a method for preparing an air sample for detection of a mixture of proteins.

20 Claims, 7 Drawing Sheets

METHOD AND SYSTEM FOR DETECTING NON-VOLATILE AND SEMI-VOLATILE ORGANIC COMPOUNDS IN MID-IR SPECTROMETRY GAS CELL CONFIGURATIONS

FIELD OF THE INVENTION

The presently disclosed subject matter relates to detection of organic compounds and their manifestation as hosts of organic compounds relevant to infectious and non-infectious disease diagnostics.

BACKGROUND

Clinical symptoms such as fever, muscle pain and fatigue are common to a large variety of diseases caused by different pathogens. For example, similar symptoms, and specifically those related to the respiratory system, are exhibited in patients infected by coronavirus disease 2019 (COVID-19), influenza, as well as many other viruses. Accordingly, as clinical evidence is insufficient, diagnostic tools are essential for identifying a specific etiological agent of a disease. Diagnostic tests are also useful in identifying recovered patients, improving the understanding of virus spreading patterns, and in monitoring the effectiveness of control measures.

Two testing techniques which are commonly used today for detecting virus infections, include genetic probes and Serodiagnosis. Genetic probes target specific DNA or RNA sequences of the virus. When carried out properly, the results of these tests are reliable. However, they may fail to detect the virus when present in extremely low levels in a patient's body and are significantly less helpful in identifying recovered patients.

Serodiagnosis is a technique that targets the antibody response to the infecting pathogen. This approach is helpful when there is difficulty in isolating the infecting agent. It is also useful in identifying past infections in case the virus is no longer present in the patient's body.

On the other hand, one disadvantage of serodiagnosis is in the time lag between the onset of infection and the development of antibodies to the infecting pathogen, a time lag which in some cases may be a few days or weeks long. A further complicating factor is that different people may have different antibody responses to a pathogen. For example, individuals with severe COVID-19 seem to develop higher antibody levels than individuals with a mild or asymptomatic disease. As a result, a test for antibodies developed using blood samples from individuals with severe COVID-19 may not work as well in detecting antibodies in people with a mild or asymptomatic version of the disease, where there are far fewer antibodies to detect.

Infection with a contagious disease does not necessarily lead to complete protection forever. With some diseases, such as measles, recovery essentially produces complete immunity to future infection for life, while recovery from other infections can be different. For example, respiratory syncytial virus—which can cause severe viral pneumonia in young children but usually only causes mild, cold-like symptoms—is so common that most infants have had it by age two. However, infection triggers only partial immunity which protects against severe disease in the future but does not protect against re-infection.

The possibility that COVID-19 infection only induces partial immunity is one important reason why it is not yet clear if "immunity passports" would work. These are meant to indicate if a person has recovered from COVID-19, cannot infect others and can go about their activities without restriction.

The global scale-up of COVID-19 diagnostic testing has been rapid, literally going from zero to over a million samples tested a day in a matter of months. This scale-up in testing has been valuable both for guiding patient care and informing public health decision-making, including on implementing physical distancing measures.

However, there have been many difficulties, especially in low- and middle-income countries. Despite the rapid scale-up in testing, demand continues to outstrip supply, and distribution of the available supply has been far from equitable across countries. Ensuring adequate test quality and reliability has been a challenge, particularly given the many manufacturers who have entered this market.

The COVID-19 pandemic as well as the global concern of microbial drug resistance, has highlighted the importance of rapid, cost effective, accurate, and non-invasive testing for pathogen infection.

The advent of molecular technologies has revealed a wealth of information about signaling pathways and gene regulation in cancer. New biomarkers and methods for classification of cancer subtypes, diagnosis, prognosis and prediction of response to therapy have been emerging. Advancements in analytical methods in molecular biology, such as polymerase chain reaction (PCR), deoxyribonucleic acid (DNA) arrays and next-generation sequencing have allowed researchers to interrogate a vast array of biological and clinical materials such as formalin-fixed, paraffin-embedded (FFPE) tissue, biopsies and cells present in blood, bone marrow or urine. Insights gained from the role and significance of the biomarkers in tumor tissues and cells will aid in understanding tumorigenesis and metastasis processes. In addition, the recent finding that circulating tumor cells (CTCs) and circulating DNA in blood can also have diagnostic value in metastatic cancers allows clinicians to use them as surrogate endpoints. Diagnostic tests based on such information could provide "real time" biopsies of cancer progression and response to therapy. These new molecular and cellular technologies will be helpful in providing more precise and objective decision-making.

On the other hand, many of the techniques that are employed today by pathologists and oncologists to generate a diagnosis, prognosis or prediction of therapy response have not changed over several decades. This fact highlights the challenges faced by new molecular and cellular technologies in having a real impact on patient management in clinic. One of the key challenges is to demonstrate the clinical value of a diagnostic test. For example, in the area of susceptibility/risk assessment, companies have commercialized molecular tests on the BRCA1 and BRCA2 genes for breast cancer. In the area of prognosis and prediction for therapy response, reverse transcription polymerase chain reaction (RT-PCR) based Oncotype Dx assay have also been adopted for breast cancer in predicting patients' benefit with chemotherapy. In addition, in situ hybridization (ISH) assays based human epidermal growth factor receptor 2 (Her-2) test and anaplastic lymphoma kinase (ALK) test have been used to predict responses to targeted therapies such as Herceptin and Xalkori in breast cancer and lung cancer, respectively. In addition to clinical value, a routine test in clinic needs to be optimized so that the assay can fit into the clinical laboratory workflow and the assay result can be generated timely and reproducibly.

A method and system for preparing a sample for the detection of proteins is disclosed in WO 2022/013877 that processes an exhaled air sample from a subject, and subjects that sample to analysis to assess the presence of certain proteins. The embodiments described herein below provide an improvement to that method and system.

SUMMARY

The presently disclosed subject matter includes a method and system for detecting, inter alia, proteins, organic compounds, as well as pathogens that cause infection including viral and microbial infections.

The disclosed method and system makes use of information extracted from exhaled organic compounds (OCs) obtained from individuals being tested for infection or screening for non-communicable diseases. Analysis of exhaled OC allows a high throughput and highly informative and non-invasive alternative to current genomics and culture-based (e.g., serodiagnosis) methods.

In accordance with one embodiment, there is provided a system that includes a pump configured to pump an exhaled air sample from a container to a cooling chamber, the cooling chamber being configured to cool the exhaled air sample to a sub-zero temperature. The system also includes an injector unit in fluid communication with the cooling chamber, an inert gas source, and a test chamber. The inert gas source is configured to supply inert gas to the injection unit at a pressure higher than the atmospheric pressure. The system further includes a heating unit configured to heat the inert gas and the test chamber.

Another embodiment includes a method for preparing an exhaled air sample for detection of a mixture of proteins in the exhaled air sample. The method includes: (a) pumping a sample comprising exhaled air from a container to a cooling chamber; (b) cooling the sample from (a) to a subzero temperature in the cooling chamber; (c) mixing in an injection unit the sample from (b) with an inert gas source at a pressure higher than the atmospheric pressure inside a test chamber, (d) heating the mixed sample to a temperature ranging from 30 to 55° C.; and (e) injecting the sample from (d) into a test chamber at a high velocity to increase the aerodynamic length and the average droplet size in the sample from (d). The method further includes analyzing the injected sample in a test chamber to detect the presence or absence of compounds of interest.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In order to understand the presently disclosed subject matter and to see how it may be carried out in practice, the subject matter will now be described, by way of non-limiting examples only, with reference to the accompanying drawings, in which:

FIG. 4 includes a schematic illustration of a pathogen testing corridor, according to some embodiments; and.

DETAILED DESCRIPTION

Figure 1A:
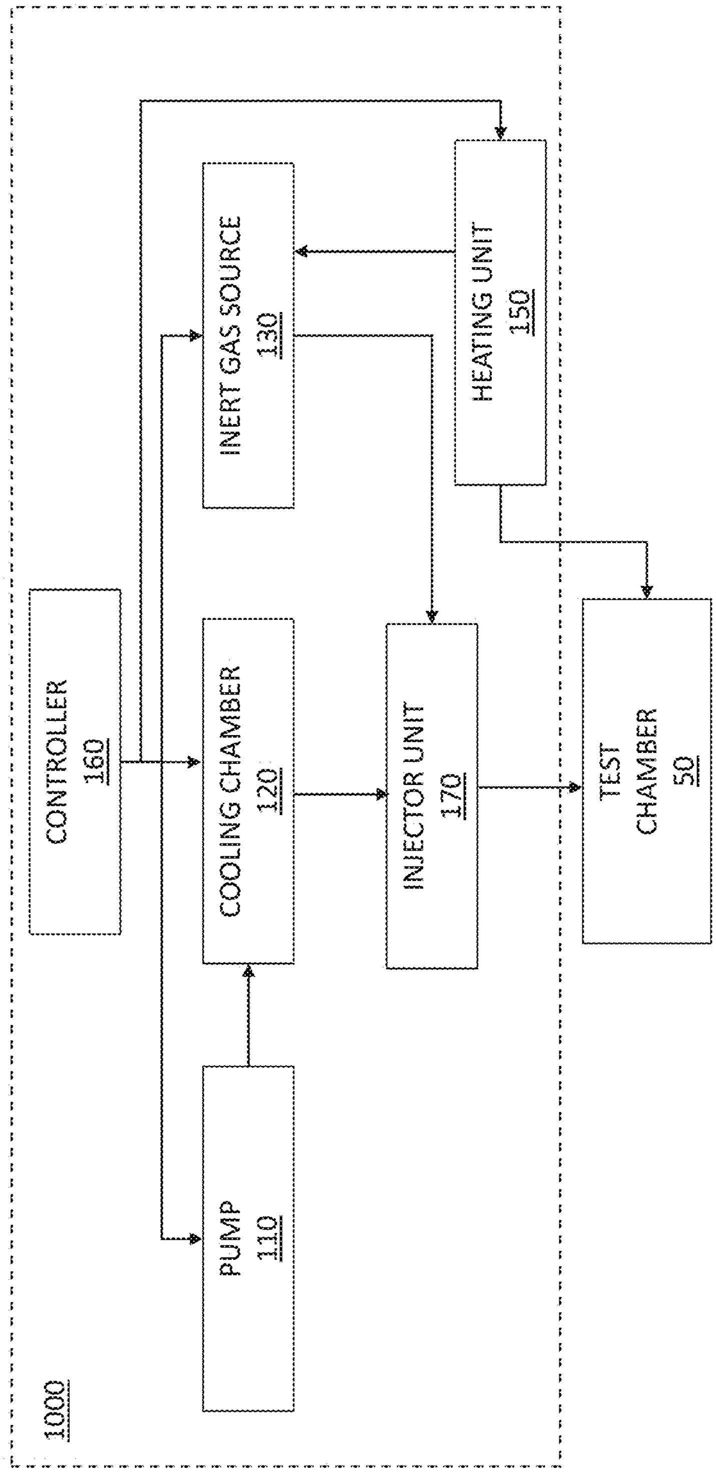
FIG. 1A includes a block diagram of a system according to some embodiments.

In the drawings and descriptions set forth, identical reference numerals indicate those components that are common to different embodiments or configurations. Elements in the drawings are not necessarily drawn to scale.

As apparent from the following discussions, it is appreciated that throughout the specification discussions utilizing terms such as "analyzing", "comparing", "determining", or the like, include an action and/or processes of a computer that manipulate and/or transform data into other data, said data represented as physical quantities, e.g., such as electronic quantities, and/or said data representing the physical objects.

The terms controller/computer/computer device/computerized device, or the like, should be expansively construed to include any kind of hardware-based electronic device with a data processing circuitry (e.g., digital signal processor (DSP), a GPU, a TPU, a field programmable gate array (FPGA), an application specific integrated circuit (ASIC), microcontroller, microprocessor etc.). The processing circuitry can comprise, for example, one or more processors operatively connected to computer memory, loaded with executable instructions for executing operations as further described below.

Controller operations in accordance with the teachings herein may be performed by a computer specially constructed for the desired purposes, or by a general-purpose computer specially configured for the desired purpose by a computer program stored in a computer readable storage medium.

As used herein, the phrase "for example," "such as", "for instance" and variants thereof, describe non-limiting embodiments of the presently disclosed subject matter. Reference in the specification to "one case", "some cases", "other cases", or variants thereof, means that a particular feature, structure or characteristic described in connection with the embodiment(s) is included in at least one embodiment of the presently disclosed subject matter. Thus, the appearance of the phrase “one case”, “some cases”, “other cases” or variants thereof does not necessarily refer to the same embodiment(s).

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination In embodiments of the presently disclosed subject matter, fewer, more and/or different stages than those shown in FIGS. 2 and 3 may be executed. In embodiments of the presently disclosed subject matter, one or more stages illustrated in FIGS. 2 and 3 may be executed in a different order and/or one or more groups of stages may be executed simultaneously. FIGS. 1B and 1C illustrate a general schematic of a system architecture in accordance with examples of the presently disclosed subject matter. Elements in FIGS. 1B and 1C may be centralized in one location or dispersed over more than one location.

Figure 1B:
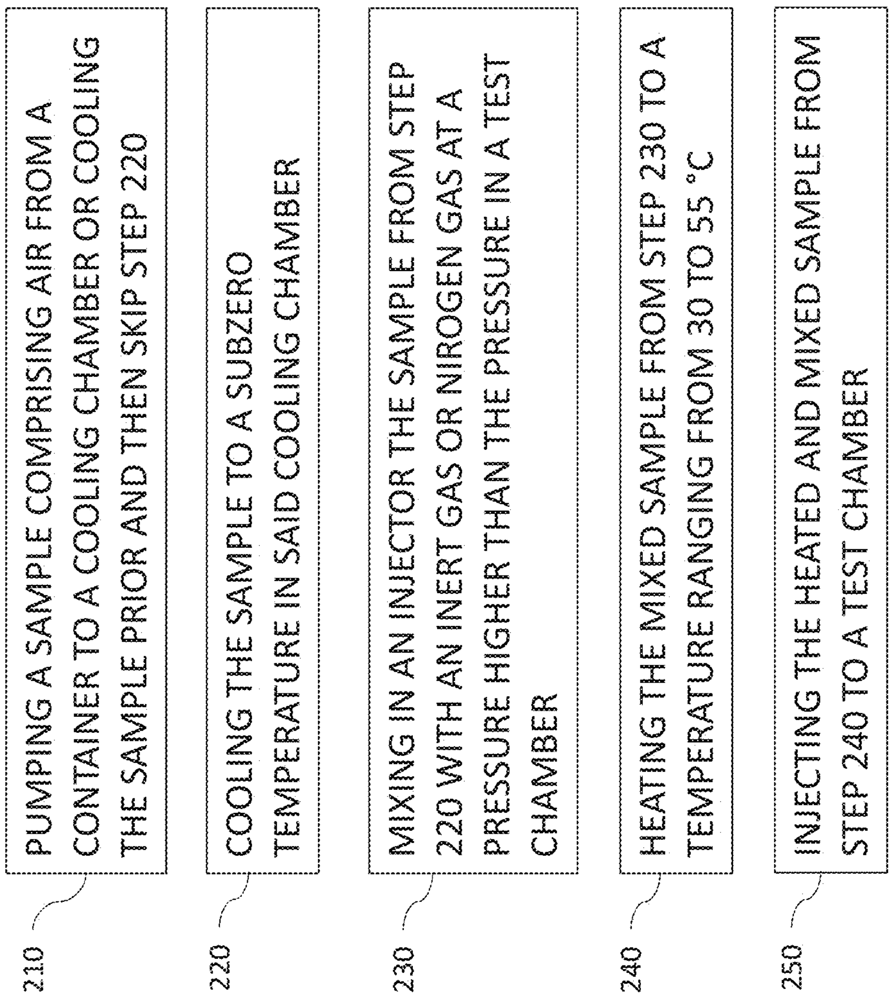
FIG. 1B includes an illustration of a flowchart of a method for preparing an air sample suitable for detection of a mixture of proteins in the air sample according to some embodiments.
Figure 1C:
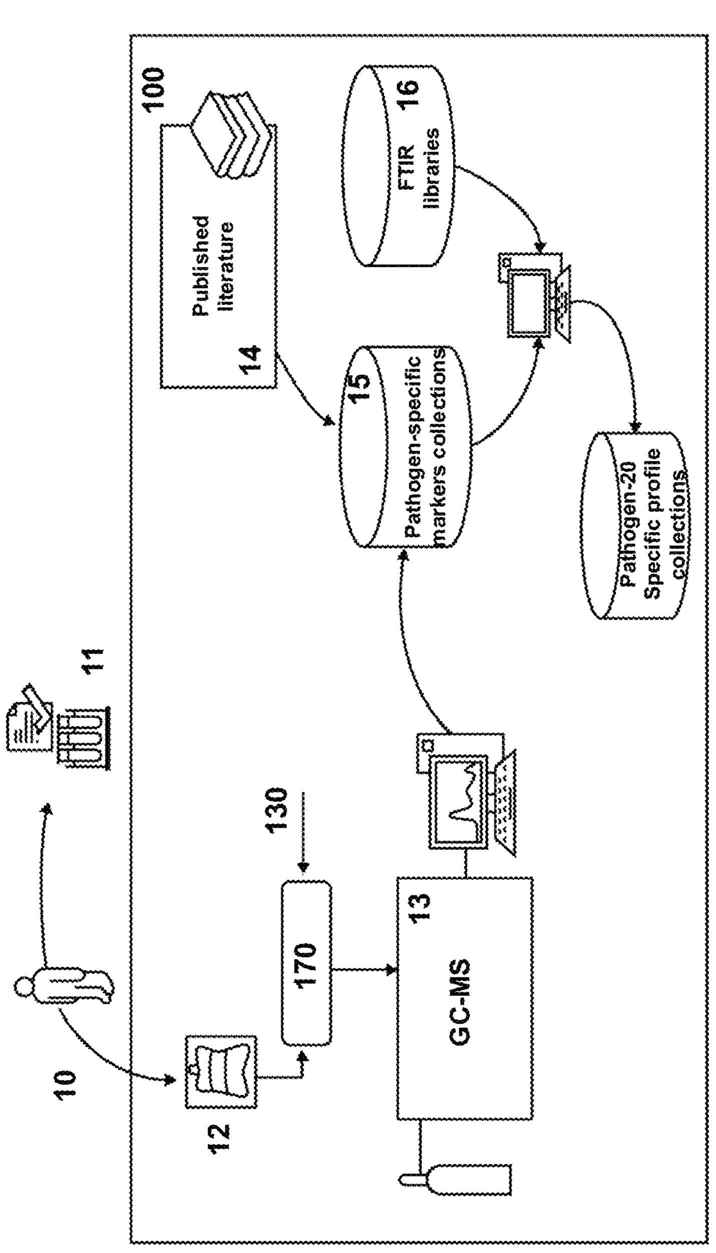
FIG. 1C includes schematic illustration of a nonlimiting example for a system for executing a learning phase, according to some embodiments FIG. 1D includes schematic illustration demonstrating a non-limiting example for a system for executing a testing phase, according to some embodiments.

Reference is made to FIG. 1A which is a block diagram of a system 1000 according to some embodiments of the invention. System 1000 may allow testing of air samples (e.g., air exhaled from a subject) at various conditions. For example, the system may improve the probability of detecting peptides, polypeptides, proteins, etc. in an exhaled air sample using a variety of analytical techniques, including gas chromatography-mass spectrometry (GC-MS), GC-FID-MS-gas chromatography-flame ionization detector-mass spectrometer, Proton-transfer-reaction mass spectrometry (PTR-TOF-MS) mid-range infrared spectroscopy and Fourier-transform infrared spectroscopy (FTIR) systems. System 1000 may be used for both the training phase and the detection phase, discussed with respect to FIGS. 1C, 1D, 2 and 3.

In some embodiments, system 1000 may include a pump 110 configured to pump an air sample, a cooling chamber 120 for cooling the air sample, an inert gas source 130, an injection unit 170, and a heating unit 140. In some embodiments, system may further include a controller 160 for controlling the controllable elements of system 1000.

In some embodiments, pump 110 may be configured to pump the air sample from a container (e.g., containers 12 and 22 illustrated in FIGS. 1C and 1D) at a capacity of at least 0.5 liter/sec, for example, 0.7 liter/sec., 0.8 liter/sec., 0.9 liter/sec., 1 liter/sec. 1.1 liter/sec, 1.2 liter/sec., 1.5 liter/sec or more. In a nonlimiting example, the container may be a sealed bag into which the user exhaled). Pump 110 may be any gas pump known in the art. In some embodiments, controller 160 may be configured to control the capacity of pump 110, for example, based on predetermined values stored in a memory associated with controller 150. Alternatively, controller 160 may be configured to control the capacity of pump 110 based on a signal received from a sensor (e.g., a flowmeter included in a pipe leading the air sample.

In some embodiments, the pumped air sample may be introduced into cooling chamber 120. Colling chamber 120 may be configured to cool the exhaled air sample to a sub-zero temperature. In some embodiments, controller 160 may control the temperature of cooling chamber 120. For example, controller 160 may execute instructions stored in a memory associated with controller 160 to cool cooling chamber 120 to a sub-zero temperature, for example, −1° C., −2° C., −3° C., −4° C., −5° C., −6° C., or lower.

In some embodiments, cooling chamber 120 may be in fluid communication with an injector unit, or injector/mixing unit 170, which in turn is in fluid communication with a test chamber 50 of a spectrometer, for example, the ionization chamber of the GC-MS, or a mid-range IR spectrometer. The pumped air sample may pass through cooling chamber 120, to be introduced into injector unit 170 at the capacity of at least 0.5 liter/sec. In some embodiments, the capacity is between 0.5 liters/sec to 10 liters/sec., for example, 0.6 liters/sec, 0.75 liters/sec., 1 liters/sec., 2 liters/sec., 5 liters/sec., and 8 liters/sec. Air sample passing through cooling chamber 120, may be dehydrated and condensed. In a nonlimiting example, the amount of water molecules in an exhaled air sample may be reduced due to the sub-zero temperature. Therefore, when ultimately injected into test chamber 50, the exhaled air sample may contain only residual amounts of water.

In some embodiments, in order to increase the mobility of large organic molecules in the air sample, (e.g., peptides, polypeptides, proteins and the like) an inert gas may be mixed with the cooled air sample from cooling chamber 120. In one embodiment, an inert gas is introduced into one end of an injector unit 170, and the cooled air sample from cooling chamber 120 is introduced into a separate opening of the injector unit 170 to permit intimate mixing. Inert gas may be supplied to injector unit 170 from inert gas source 130 at a pressure higher than the atmospheric pressure, and at a pressure higher than the pressure in the test chamber 50. Inert gas source may include a pressurized gas tank and/or a condenser for supplying the inert gas to test chamber 50 at pressure higher than the atmospheric pressure. In some embodiments, the inert gas may be supplied at a pressure of 1.1 atm. to 2.5 atm., for example, 1. 1 atm., 1.1 atm., 1.2 atm., 1.3 atm, 1.4 atm., 1.5 atm, 1.7 atm., 2 atm., and more. In some embodiments, controller 160 may control the timing, duration and/or pressure of the inert gas supply to test chamber 50, for example, based on instructions stored in a memory associated with controller 160.

In some embodiments, the inert gas may be characterized by being undetectable by a Mid IR spectrometry. For example, the inert gas may be nitrogen or helium which are undetectable by Mid IR spectrometry.

Figure 5:
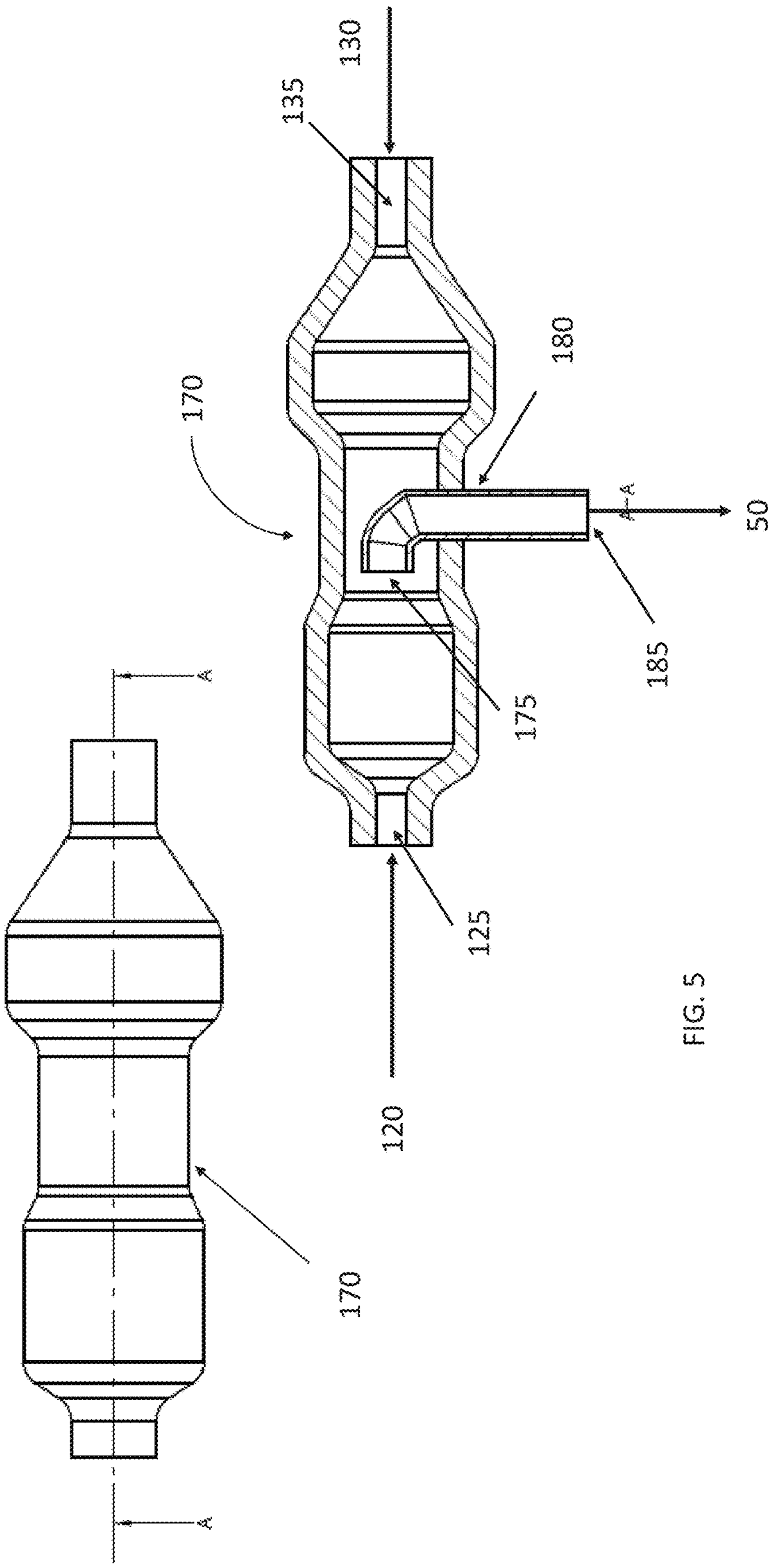
FIG. 5 is an illustration of an injector for use in the embodiments.

In an embodiment, injector unit 170, as illustrated in FIG. 5, includes two inlets 125, 135 in communication with: (a) the cooled air sample from cooling chamber 120; and (b) the inert gas from inert gas source 130. While FIG. 5 illustrates the respective air flows entering the injector unit 170 from opposite ends of a longitudinal axis-a of the injector unit 170, their entry points could be positioned elsewhere along the perimeter of injector unit 170. Generally facing inlet 125 is an entry inlet 175 for the outlet conduit 180 of injector unit 170 that provides the mixed air to test chamber 50. Outlet conduit 180 may be comprised of a curved tubular segment, and may have its entry inlet 175 positioned within the body of injector unit 170, and its mixed air outlet 185 positioned outside the body of injector unit 170 to provide the mixed air to test chamber 50. While not wishing to be bound by any theory of operation, it is believed that the use and design of injector unit 170 intimately mixes the cooled air sample and the inert gas, and injects the mixed air sample to test chamber 50 at a high velocity, thereby increasing the aerodynamic length and the average droplet size in the mixed air sample. This is believed to permit the droplets to remain in test chamber 50 for longer periods of time, thereby enhancing the resolution of the analyzer used in test chamber 50, and providing for the use of less sensitive analyzers. In addition, extending the aerodynamic length of the mixed air sample permits the detection of organic compounds that may not be volatile.

In one embodiment, the injector unit 170 injects the mixed air sample into test chamber 50 at a velocity of from about 3 to about 15 liters per minute (lpm), or from about 4 to about 10 lpm, or from about 4 to about 9 lpm, or from about 5 to about 7 lpm. In other embodiments, inlets 125 and 135 having an inner diameter of from about 1 mm to about 20 mm, or from about 2 mm to about 15 mm, or from about 3 mm to about 7 mm, or about 4 mm. In another embodiment, the inner diameter of entry inlet 175 is smaller than the inner diameter of inlets 125, 135, which provides for adequate mixing of the cooled air sample and the inert gas. By mixing the respective air sample and injecting them at high velocity to test chamber 50, the droplets remain in test chamber 50 for a period of from about 1.75 to about 5 minutes, or from about 2 to about 4 minutes, or up to 3 minutes. Samples fed directly to an analyzer without an injector unit 170, or with prior injectors, remained in the test chamber for significantly shorter periods of time, such as up to about 45 seconds.

In some embodiments, to further provide kinetic energy to the large organic molecules in the air sample, the cooled air sample mixed with the inert gas in injector unit 170 may be heated. In some embodiments, heating unit 140 may heat the mixed air sample and inert gas, either by providing heat to injector unit 170, test chamber 50, or by providing heat to the inert gas. For example, heating unit 140 may include heating coils located in close proximity to injector unit 170 and/or test chamber 50 (e.g., 1-5 mm from the external walls of injector unit 170 and/or test chamber 50) in order to convey heat to injector unit 170 and/or test chamber 50. In some embodiments, heating unit 140 may further include a fan for increasing the conveying of heated air towards injector unit 170 and/or test chamber 50.

Additionally, or alternatively, heating unit 140 may include one or more heating elements adopted to heat the inert gas prior to the provision of the gas to injector unit 170. In some embodiments, heating elements, such as, heating coils may be placed in proximity (e.g., 1-5 mm) to a tube supplying the inert gas from source 130 to injector unit 170. For example, the coils may encompass the gas tub, placed near the walls of the gas tube and the like.

In some embodiments, heating unit 140 may include one or more thermometers (e.g., one or more thermocouples) for measuring the temperature of injector unit 170 and/or test chamber 50 and/or the air sample. In some embodiments, controller 160 may control the level and/or duration of power provided to the heating elements according to measurements received from the one or more thermometers. In some embodiments, controller 160 may control heating unit 140 to heat the mixed air sample to a temperature of 30 to 55° C. In some embodiments, controller 160 may control heating unit 140 to heat the injector unit 170 to a temperature of 30 to 55° C. In some embodiments, controller 160 may control heating unit 140 to heat the test chamber 50 to a temperature of 30 to 55° ° C. In some embodiments, controller 160 may control heating unit 140 to heat the inert gas to a temperature of 30 to 55° C.

Controller 160 may include any computing device configured to execute methods according to the embodiments described herein. Controller 160 may include a processor and a memory. In some embodiments, the processor may be configured to execute instructions stored in the memory.

Reference is now made to FIG. 1B which is a flowchart of a method for preparing an air sample for detection of a mixture of proteins in the air sample, according to some embodiments of the invention. The method of FIG. 1C may be performed by system 1000, under the control of controller 160. In step 210, a sample comprising air may be pumped, for example, by pump 110 from a container (e.g., containers 12 and 22 illustrated in FIGS. 1C and 1D) to cooling chamber 120. In some embodiments, the air sample may be pumped at a capacity of between 0.5 liters/sec to 10 liters/sec. FIG. 1C illustrates pumping the cooled air sample to injector unit 170 where it is mixed with inert gas 130, and injected to test chamber 50, which includes, for example, a GC-MS device 13. The same arrangement may exist with respect to FIG. 1D, although the injector unit 170 is not illustrated therein.

In step 220, the air sample may be cooled in cooling chamber 120 to a subzero temperature. Form cooling chamber 120, the air sample may be introduced to an injector unit or injector and then injected into test chamber (e.g., test chamber 50) to be analyzed for the presence of proteins.

In step 230, the air sample may be mixed with an inert gas at a pressure higher than the atmospheric pressure, and higher than the pressure inside the test chamber (e.g., test chamber 50). In some embodiments, the inert gas is supplied at a pressure of between 1.1 atm. to 2.5 atm.

In step 240, the mixed sample may be heated to a temperature ranging from 30 to 55° C. For example, heating unit 140 may heat injector unit 170 and/or test chamber 50 and/or the inert gas provided to injector unit 170, as discussed herein above.

Figure 2:
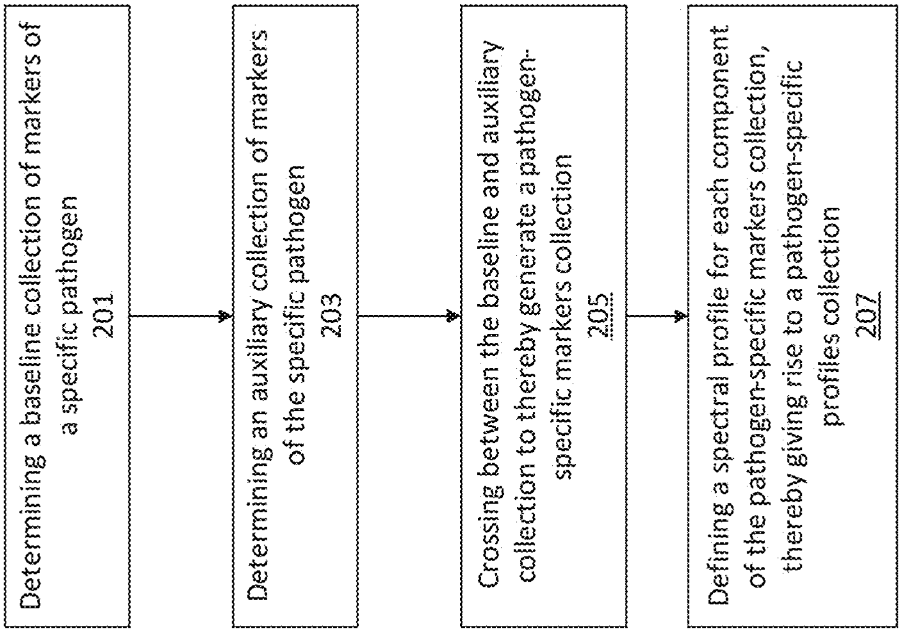
FIG. 2 includes a flowchart illustrating a non-limiting example for operations performed during a learning phase, according to some embodiments.

Bearing the above in mind, attention is brought to FIG. 1C schematically illustrating a non-limiting example for a system (100) for executing a learning phase, according to some examples of the presently disclosed subject matter. FIG. 2 is a flowchart illustrating a non-limiting example for operations performed during a learning phase, according to some examples of the presently disclosed subject matter. For better clarity and by way of example, operations in FIG. 2 are described herein with reference to system 1000.

Exhaled VOCs and non-volatile organic compounds of different patients infected by different pathogens generally contain a different combination of organic compounds (referred to herein also as "markers") resulting from the specific mechanism of action of each pathogen.

As disclosed herein, below a combination of markers that are uniquely present in patients infected by a specific pathogen can be found. Once identified the combination of markers (referred to herein after as "pathogen-specific markers collection") can be used as identifiable signature being indicative, when detected in an individual, of an infection of the individual with the specific pathogen (e.g. COVID-19). As further explained herein below, during the learning phase pathogen-specific markers collections and respective pathogen-specific profiles collections are determined.

Figure 1D:
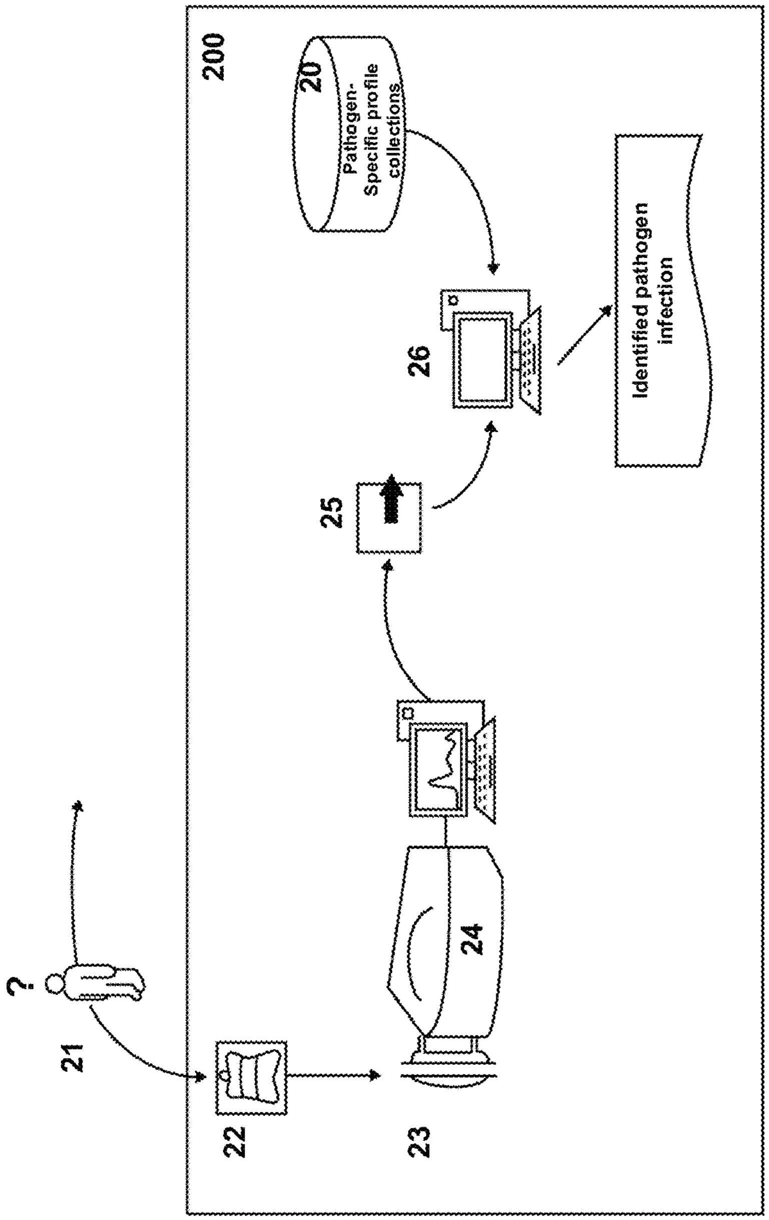

Referring now to FIGS. 1C, 1D, and FIG. 2, at block 201, a baseline collection of markers identified in patients infected by a specific pathogen or Non-communicable disease is determined. To this end, exhaled OC (12) is obtained from patients (10) tested positive for the pathogen using other diagnostic methods such as PCR, or serological tests or other gold standard test (11). The exhaled air is analysed using for example gas chromatography-mass spectrometry (GC-MS), GC-FID-MS-gas chromatography-flame ionization detector-mass spectrometer, Proton-transfer-reaction mass spectrometry (PTR-TOF-MS) mid-range infrared spectroscopy and Fourier-transform infrared spectroscopy (FTIR) systems, and organic compounds found in the tested patients are identified. FIG. 1*a*, shows by way of example GC-MS device (13) used for analysing the exhaled air sample held in a container (12).

A collection of organic compounds, which are found in a significantly different concentration in patients infected by the specific pathogen as compared to their concentration in control samples, obtained for examples from individuals infected by a different pathogen or from healthy individuals. For example, in the case of COVID-19, the samples can be compared to those of patients infected by a different pathogen causing a lung disease, e.g., tuberculosis. As further specified below the collection of compounds (or markers) can be divided into several groups or non-communicable diseases.

In some examples, an auxiliary collection of markers is also determined (block 203). The auxiliary collection can be obtained, for example, from published literature (14) of previous research of exhaled compound analysis extracted from patients infected by the specific pathogen (e.g., COVID-19) or non-communicable diseases or disorders.

At block 205, the baseline markers collection can be crossed with the auxiliary markers collection and overlapping markers found in both groups identified, giving rise to a "pathogen-specific markers collection." The pathogen-specific markers collection can include markers that are uniquely found in individuals infected by a specific pathogen. In some examples, a combination of at least three markers, each from a different marker group, can be used.

Notably, according to current research and practice, only a limited group of markers are used for identifying infections using exhaled air samples. These groups include Oxides, Fatty acids, Alkanes, Non-Alkanes and proteins. The methods and systems disclosed herein provide for (inter alia, by crossing between the baseline markers collection and auxiliary markers collection) the identification of new collections of overlapping markers that were previously unknown as markers.

A non-exhaustive list of possible combinations of markers from different groups that are suggested herein as pathogen-specific markers collection for identifying specific pathogen infection is disclosed herein below: Oxides./Ketones/Proteins/Fatty Acids, Oxides./Ketones/Proteins/Lipids, Oxides./Ketones/Proteins/Cytokines, Ketones/Proteins/Fatty Acids/Lipids, Oxides./Proteins/Fatty Acids/Lipids, Ketones/Proteins/Fatty Acids/cytokines, Oxides./Proteins/Fatty acids/Cytokines, Ketones/Proteins/Lipids/Cytokines, Oxides./Proteins/Lipids/Cytokines, or any other combination of the groups Ketones: Acetaldehyde, propanal, n-propyl acetate, methyl methacrylate, styrene and 1,1-dipropoxypropane or others.

Proteins: IL-6, PCT, CRP or others.

Fatty Acids, Lipids and Cytokines.

In some examples, the baseline markers and auxiliary markers are stored on a computer storage device and a processing circuitry is used for comparing the two groups and providing an output comprising a group of overlapping markers. In some examples, the resulting pathogen-specific markers collection is stored in database of some sort (e.g., table of a relational database) on a computer storage device (15), as shown in FIG. 1C.

In some examples, personal information of the tested patients (used for creating the baseline markers) including for example, age, sex, education, residential address, prescribed medications, etc., is also collected and added to the database (15). Since personal information in general and specifically medication being administered to an individual, may influence the concentration of the markers found in the subject's exhaled air, this data is also collected in order to correlate between variations in the concentration of markers and personal information, thus providing a more accurate index of markers collections. For example, lipids expression is expected to be lower in VOC samples obtained from individuals being administered with lipid lowering medication such as statins, as compared to other individuals in the population that do not use this drug regularly. Personal information can be obtained for example, from electronic medical records of the patient or with the help of questionnaires provided to the subjects.

Furthermore, in some cases of pathogen infection, some organic components may be present in individuals during a specific phase of the infection and not in other phases. Accordingly, information about the specific phase of the infection is obtained (e.g., by other robust testing methods and/or by interviewing the subject and/or a physician treating the patient) and is added to the database (15). This information allows to correlate between pathogen-specific markers collections and phases of the respective infection, possibly allowing to identify sub-categories of markers collection indicative of different phases of the same infection. For example, individuals infected by the same pathogen may exhibit a first pathogen-specific markers collection during the initial infection-phase, a second and different than the first pathogen-specific markers collections during the middle infection-phase, and a third, different than the first and second, pathogen-specific markers collections, during the last and final infection-phase.

At block 207, a spectral profile is defined for each component of the pathogen-specific markers collection, thereby giving rise to a pathogen-specific profiles collection. The spectral profile of each component usually is a spectroscopic readout of the component when analyzed using a spectroscopic device such as Fourier Transform Infrared Spectroscopy (FTIR), or other similar device. Since every molecule has a unique structure that produces a unique spectroscopic readout, the pathogen-specific spectral profile comprises a plurality of unique spectroscopic readouts (e.g., transmission curves), each of a respective marker in the collection.

In some examples, where multiple pathogen-specific markers collections are determined, a corresponding pathogen-specific profiles collection is determined for each one of them. The different pathogen-specific markers collections and pathogen-specific profiles collection can be stored in library stored in a computer data-storage device.

In general, each manufacturer of a spectroscopic device, (e.g., an FTIR device), provides libraries specifying the spectral profiles (and signatures) obtained by the device for a large variety of materials. These libraries (16) can be used for constructing the pathogen-specific profiles collection. The spectral profiles of each component of a pathogen-specific markers collection can be retrieved from the libraries provided by the manufacturer of the specific spectroscopic device that is intended to be used during the testing phase as described below. According to some examples, a processing circuitry is configured to automatically match between components of each pathogen-specific profiles collection, as determined based on GC-MS data and the respective spectral profile obtained from FTIR libraries.

It is noted that while the following description predominantly refers to FTIR, the presently disclosed subject matter should not be construed to be limited to using FTIR alone and other suitable spectroscopic methods, including mid-IR spectroscopy, are contemplated with the scope of the disclosed matter as well.

As further described below, according to the presently disclosed subject matter, the collection of spectroscopic readouts, each corresponding to the optical response of a respective component in the pathogen-specific markers collections, is used as a unique identifier for detecting individuals infected by the specific pathogen (e.g., COVID-19).

Figure 3:
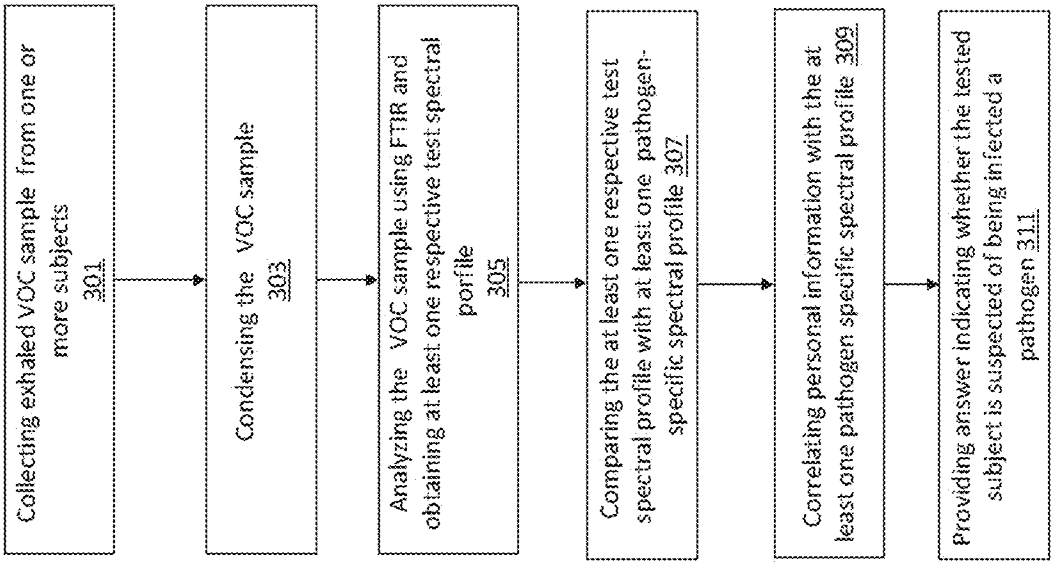
FIG. 3 includes a flowchart illustrating a non-limiting example for operations performed during a testing phase, according to some embodiments.

FIG. 1D schematically illustrates a non-limiting example for a system (200) configured for executing a testing phase, according to some examples of the presently disclosed subject matter. FIG. 3 is a flowchart of a non-limiting example for operations performed during a pathogen testing phase, according to examples of the presently disclosed subject matter. For better clarity and by way of non-limiting example only, operations in FIG. 3 are described herein with reference to system 200.

At block 301 exhaled VOC is collected from a subject (21). While FIG. 3 lists exhaled VOC, the embodiments described herein provide for the testing and analysis of compounds in exhaled air, in addition to VOCs. For purposes of clarity and by way of non-limiting example, FIG. 3 refers to the exhaled air as containing exhaled VOC. In some examples, the subject is an individual suspected of being infected with a specific pathogen. In other examples, the subject is an individual suspected of being infected with some pathogen without knowing its specific nature.

Exhaled VOC (including exhaled compounds other than VOCs) can be collected using a breath sampling kit VOC and airbag. One example is RTubeVOC™ End Tidal Air Collector manufactured by Respiratory Research.

At block 303, the exhaled air sample (including exhaled VOC and compounds other than VOCs) held in a container (22) obtained from a subject is analyzed using a spectroscopic device (24) such as FTIR, as shown in FIG. 1D. It will be understood that the exhaled air from container 22 is mixed with an inert gas in injector unit 170, and then injected into the spectroscopic device (24) present in the test chamber 50. The spectrographic readings include a spectral profile of the air sample collected from the subject (referred to herein as "group of test spectral profiles"). Each group of test spectral profiles comprises multiple readings (individual spectral profiles) obtained for different components in the exhaled air sample.

When compared to chromatography-mass spectrometry methods (e.g., GC-MS, GC-FID-MS, SPME-GC-MS, PTR-TOF-MS etc.), spectroscopic methods are simpler, more easily applied, provide a more rapid response and are generally less expensive. Therefore, spectroscopic methods are more suitable as a mass/high throughput testing tool. On the other hand, spectroscopic methods are in general less sensitive than chromatography-mass spectrometry methods and therefore provide less accurate results. As mentioned previously, however, the use of the injector unit 170 increases the aerodynamic length of the air sample, which increases the average droplet size so they remain in the analyzer longer. This permits the use of less sensitive analyzers, while providing higher resolution than the analyzer without the injector unit 170. According to one embodiment, the injector unit 170 can be used to "retrofit" an existing or "off-the-shelf" analyzer, thereby providing an improved analyzer with greater sensitivity and higher resolution than the existing or off-the-shelf analyzer.

According to some examples of the presently disclosed subject matter exhaled air samples obtained from a subject are condensed and the condensed air samples are analyzed using spectroscopic method e.g., FTIR, mid-range IR, etc., to obtain a group of test spectral profiles (block 305). Since water is expected to be condensed faster than other gases present in the air sample, the condensate would include a higher concentration of the sought-after markers and the signal to noise ratio between the compounds of interest and water in the sample would be reduced. As a result of increasing the concentration of the markers, it is made possible to use a spectroscopic method such as mid-range IR, and/or FTIR that provide acceptable accuracy.

Condensation can be accomplished using a condenser (23), where air sample is delivered through the condenser before entering the injector unit 170, and then injected into analyzer 24. According to another example, a cooling chamber 120 may be used, as shown in FIG. 1A. The cooling chamber 120 may include a surface that can be cooled down to temperatures below 0 Celsius (e.g., −60° C.), the surface is configured to accommodate the exhaled air sample during the analysis.

According to further examples of the presently disclosed subject matter, a cooling chamber separate from cooling chamber 120 is disclosed herein. The cooling chamber may include a surface configured to hold the sample during analysis in analyzer 24. The chamber can be designed to be isolated from the external environment in order to reduce heating. The chamber can include an opening for injecting the mixed air sample from injector 170. According to one example, a cooling agent in gaseous state (e.g., liquid nitrogen gas) is blown into the chamber and onto the surface along with the insertion of the mixed air sample and its placement on the surface (which can be inserted from a different opening) thereby cooling the sample and causing condensation. According to a further example, the air sample may be inserted into the chamber and onto the surface by blowing the cooling agent through an opening and allowing the air sample to flow with the cooling agent into the chamber. The cooling agent can be continuously delivered into the chamber during the entire analysis to maintain the cooling throughout the entire process. In cases where different air samples are tested one after the other, the cooling agent can be continuously delivered into the chamber in order to maintain the low temperature required for condensation for all samples.

At block 307 and as illustrated in FIG. 1D, a group of test spectral profiles (25) is compared to at least one pathogen-specific spectral profile (20) in search for correlation. A match between the two profiles indicates that the tested subject is suspected of being infected by the specific pathogen.

In some examples, where multiple pathogen-specific markers collections are determined, the group of test spectral profiles can be screened against a corresponding library of pathogen-specific spectral profiles in search for a matching profile. In case a match is found the subject is classified as suspected of being infected by the respective pathogen of the matching profile. Thus, the presently disclosed subject matter provides a pathogen diagnostic tool to rapidly screen a tested subject for a plurality of pathogens using a single exhaled air sample. Notably, as explained above, in addition to different pathogen-specific spectral profiles for different pathogens, there may be more than one pathogen-specific spectral profile for the same pathogen, e.g., each indicative of different infection phase.

According to some examples, a processing circuitry (e.g., on device 26) is configured to perform the matching between the profiles in the group of test spectral profiles and one or more pathogen-specific spectral profiles.

As mentioned previously, personal information can be correlated with the pathogen-specific spectral profiles in order to be able to perform more accurate detections (block 309).

At block 311 an answer is provided. The specific output of the process may vary. According to one example, where the subject is tested for being infected by a specific pathogen, the output can include data indicating whether the subject is suspected as being infected or not. The output can include a positive or negative answer, where positive is given when the probability that the subject is infected is above a certain threshold value. Probability can be determined based on the correlation between the pathogen-specific spectral profile of the tested pathogen and the group of test spectral profiles.

For example, assuming a given pathogen-specific spectral profile comprises four individual spectral profiles, each of the different organic components, the spectral response of each component representing an expected spectral profile, is compared to a respective tested spectral profile obtained from the exhaled air of the tested individual. One approach of scoring the correlation of the spectral profiles between the tested sample and the expected may be based on the number of spectral profiles that show correlation above a certain threshold.

In case the subject's exhaled air is screened against a library comprising two or more pathogen-specific spectral profiles, the correlation between each one of the pathogen-specific spectral profile and the tested spectral profile is determined and the pathogen-specific spectral profile that exhibits the highest correlation, which is also greater than a certain minimal threshold, servers to indicate that the subject is infected (or suspected of being infected) by the respective pathogen. In some examples, more than one pathogen can be identified, in case the correlation score of more than one pathogen-specific spectral profile is above threshold.

According to some examples, pathogen-specific markers collections are divided into different types, where types include for example: a first type of markers collections (pathogen-specific markers collection) indicative of the presence of a specific pathogen; and a second type of markers collections indicative of an infection progression (phase). The second type of markers collections can be either pathogen specific or it can be relevant to more than one pathogen.

One example of the system and method described herein may include, for example, the following six (6) markers groups:

(1) Fatty Acids or lipids—presence in an air sample indicates a viral proliferation phase as cells disintegration is starting in the lungs; applies to all viral infections;

(2) Nitric oxide (NO) and Isoprene—presence in an air sample indicates an occurring or imminent oxidative stress. In COVID19 presence is detected early on sometime from day 4;

(3) Alkanes—normally detected early as a precursor to immune system activation from around day 2; applies to all viral infections;

(4) Non-Alkanes—normally detected from day 4 and on; indicate active immune system response; applies to all viral infections;

(5) Proteins—normally detected early on; indicates early detection of a pathogen by the immune system; generates specific spectral profiles according to virus type or bacteria; and (6) Cytokines—presence in an air sample indicates an immune system attack on pathogen; usually overly expressed in COVID19.

By correlating an exhaled air sample content to the above group, the resulting combination of identified markers (e.g., identified spectral profiles) can be used for profiling an infection with specific information.

The air sample may be analyzed by FTIR, and the identified spectral profiles are compared to a library of spectral profiles. Each spectral profile provides specific information about the infection. In the above example, correlation to markers from groups 2, 5, and 6 is indicative of COVID19 infection. Correlation to markers from groups 3 and 4 would add data indicating the infection phase, e.g., whether early (up to four days) or later in the infection cycle. Correlations to markers from group 1 will add data about contagious stage.

The correlation between pathogen-specific spectral profiles and pathogen infection characteristics is improved as more data from more subjects is accumulated. Machine learning can be applied on the data in order to further improve the correlation and reduce the number of components in each collection to create smaller sets to enable detection and classification of pathogen infection with less information and in shorter time. Detections and characterization of pathogen infections as disclosed herein can be followed by applying other robust detection methods (e.g., PCR) on the tested individuals and using the results from these tests as feedback for confirming the validity of the tests and applying changes to the various profiles if needed.

The presently disclosed subject matter further contemplates a method of testing multiple subjects e.g., a crowd of subjects, simultaneously. According to some examples, exhaled air samples are taken from a closed space where multiple people are present, e.g., a closed room or chamber. The air samples are tested as described above with reference to FIG. 3 and in case it is tested positive to a pathogen (e.g., COVID-19), all the people that were present in the closed space are suspected as being infected by the pathogen.

Figure 4:
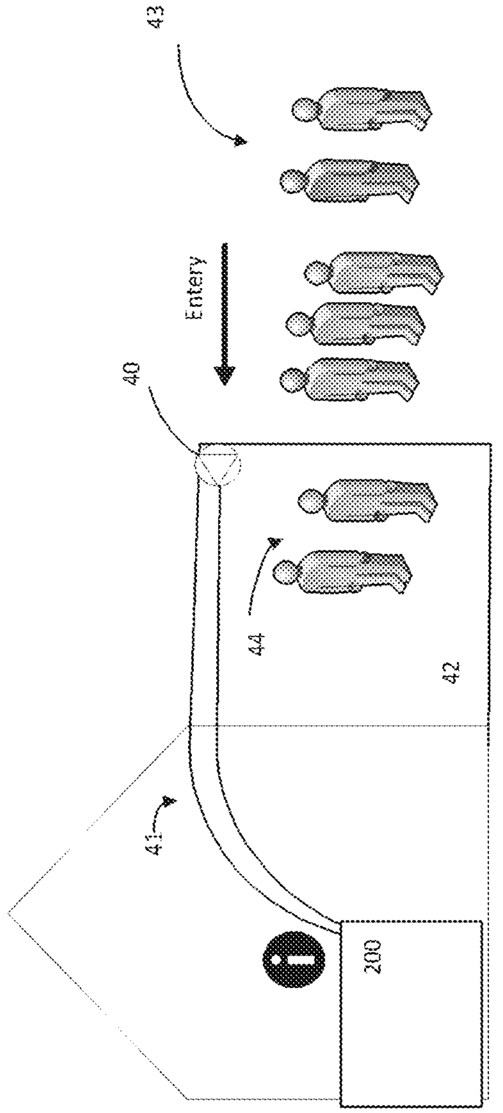

FIG. 4 is a schematic illustration of a pathogen detection chamber, according to some examples of the presently disclosed subject matter. A pathogen detection chamber (42) can be a closed space such as a room, part of room or some other designated chamber. For example, a chamber can be made as a plastic (e.g., inflatable plastic) corridor a few meters long (e.g., 1-2 meters) having an entry and an exit. The size of the corridor can be adapted to fit a maximal number of persons, e.g., one person, two persons, 3 persons, etc.

In some embodiments, the detection chamber (42) can be set or placed, for example, at a public location where people are passing. For example, at the entry to a building such as an airport or hospital, where people are directed to pass through the corridor. For example, if the corridor is placed at the entry to a building anyone that wishes to enter the building (43) must pass through the corridor. The corridor can be designed as a sealed or at least partly sealed structure to avoid entry of ambient air. In some examples, an air blower can be attached to the corridor in order to blow clean air (e.g., disinfected air) into the corridor. In some examples, other measures can be applied to reduce entry of ambient air into the corridor and thus reduce contamination of exhaled air samples from the individuals (43).

A pump (40) for pumping air (e.g., VOC and non-VOC samples) from inside the corridor (42) is attached to the corridor and the air is lead through a tubing system (41) to system 200 in FIG. 1D (or 1,000 in FIG. 1A, or 100 in FIG.

1C). In some examples the pump can be placed at the upper part of the corridor or at its side or on the floor. In other examples several pumps can be placed at different places all connected by tubing to a main tube leading the air to system 200 in FIG. 1D (or 1,000 in FIG. 1A, or 100 in FIG. 1C).

As explained above, system 200 can comprise a condenser of some type. In some examples the air is led through the tubing system and is blown through the tubing system into a cooling chamber of the analyzer together with a gaseous cooling agent, e.g., gaseous liquid nitrogen. The cooling agent can be delivered into the analyzer via an opening in the cooling chamber, in order to allow continuous cooling of incoming air samples from the corridor (42).

The exhaled air obtained from the corridor is analyzed using system 200 as described above with reference to FIG. 3. In the event system 200 positively identifies the existence of a pathogen-specific spectral profile in the tested air sample, one or more individuals that were inside the corridor during the time the exhaled air sample was obtained are delayed for further investigation and testing. Since it may not always be certain who exactly is the infected person, in some examples, several people that passed through the corridor, within a certain time period from the time of positive identification of a pathogen-specific spectral profile, can be delayed for further testing.

According to some embodiments, there is provided a method for preparing an air sample for detection of a mixture of proteins in the air sample. In some embodiments, preparing an air sample according to the herein disclosed method renders or provides an air sample suitable for detection or determination of the presence of a mixture of proteins in the air sample, as described herein.

As used herein, the terms "peptide", "polypeptide" and "protein" to refer to a polymer of amino acid residues. In another embodiment, the terms "peptide", "polypeptide" and "protein" as used herein encompass native peptides, peptidomimetics (typically including non-peptide bonds or other synthetic modifications) and the peptide analogues peptoids and semipeptoids or any combination thereof. In another embodiment, the peptides polypeptides and proteins described have modifications rendering them more stable while in the body or more capable of penetrating into cells. In one embodiment, the terms "peptide", "polypeptide" and "protein" apply to naturally occurring amino acid polymers. In another embodiment, the terms "peptide", "polypeptide" and "protein" apply to amino acid polymers in which one or more amino acid residue is an artificial chemical analogue of a corresponding naturally occurring amino acid.

In some embodiments, a peptide comprises a chain of 2 to 50 amino acids. In some embodiments, a peptide is up to 50 amino acids long. In some embodiments, the terms "polypeptide" and "protein" are used herein interchangeably. In some embodiments, a "polypeptide" and/or a "protein" comprises at least 50 amino acids. In some embodiments, a "polypeptide" and/or a "protein" comprises multiple peptide subunits.

In some embodiments, the method includes: (a) pumping a sample comprising exhaled air from a container to a cooling chamber; (b) cooling the sample from (a) to a subzero temperature in the cooling chamber; (c) mixing in an injection unit the sample from (b) with an inert gas source at a pressure higher than the atmospheric pressure inside a test chamber, (d) heating the mixed sample to a temperature ranging from 30 to 55° C.; and (e) injecting the sample from (d) into a test chamber at a high velocity to increase the aerodynamic length and the average droplet size in the sample from (d). The method may further includes analyzing the injected sample in a test chamber to detect the presence or absence of compounds of interest.

In some embodiments, heating comprises subjecting to, bringing to a temperature of, or both, at least about 30° ° C., at least about 35° C., at least about 40° C., at least about 45° C., at least about 50° C., at least about 55° C., at least about 60° C., at least about 65° C., or any value and range therebetween. Each possibility represents a separate embodiment. In some embodiments, heating comprises subjecting to, bringing to a temperature in, or both, a range of about 30 to about 65° C., about 35 to about 60° C., about 40 to about 65° C., about 45 to about 60° C., or about 37 to about 52° C. Each possibility represents a separate embodiment.

In some embodiments, step (c) of the herein disclosed method provides or results with an air sample suitable for the detection and/or determination of a mixture of proteins in the air sample. In some embodiments, the method further comprises a step (f) comprising determining a spectral profile of the sample from step (e) and comparing the spectral profile to a reference profile.

In some embodiments, a correlation of at least 30%, 40%, 50%, 60%, 70%, 80%, 90%, 95%, 97%, 99%, or 100% between the spectral profile and the reference profile is indicative of the presence of the mixture of proteins in the air sample, or any value and range therebetween. Each possibility represents a separate embodiment. In some embodiments, a correlation of 30-100%, 40-100%, 50-100%, 60-100%, 70-100%, 80-100%, 90-100%, 95-100%, 97-100%, or 99-100% between the spectral profile and the reference profile is indicative of the presence of the mixture of proteins in the air sample. Each possibility represents a separate embodiment. In some embodiments, a correlation of less than 1%, 5%, 10%, 15%, 20%, 25%, or 30% between the spectral profile and the reference profile is indicative of the absence of the mixture of proteins in the air sample, or any value and range therebetween. Each possibility represents a separate embodiment. In some embodiments, a correlation of 1-29.9%, 1-29%, 1-25%, 1-20%, or 0.5-28%, between the spectral profile and the reference profile is indicative of the absence of the mixture of proteins in the air sample. Each possibility represents a separate embodiment.

In some embodiments, the presence of a mixture of proteins in an air sample derived or obtained from a subject, being determined according to the method described herein, is indicative of the subject being afflicted with a disease or a condition, including a pathogen inducing same (e.g., also may referred to "positive").

In some embodiments, the absence of a mixture of proteins in an air sample derived or obtained from a subject, being determined according to the method of the invention, is indicative of the subject not being afflicted with a disease or a condition, including a pathogen inducing same (e.g., also may referred to "negative").

In some embodiments, "correlation" as used herein refers to similarity or identity to a predetermined threshold or reference pattern or spectra. In some embodiments, "correlation %" as used herein refers to the peaks (e.g., representing identified compounds or molecules) of the spectral profile of the sample that are shared with the reference profile, or identical thereto.

In some embodiments, increased correlation % refers to a case wherein an increased number of peaks is shared or identical for the spectral profile of the sample and the reference profile.

In some embodiments, increased correlation % refers to the similarity or identity of an air sample prepared according to the method of the invention to a predetermined or known reference sample, e.g., the reference profile, as described herein.

In some embodiments, the more the spectral profile of the sample is similar or identical to the reference profile, the correlation increases.

In some embodiments, the term "correlation" as used herein indicates the level of similarity or identity of proteins' profile of the sample to the proteins' profile of the reference. In some embodiments, the term "correlation" as used herein indicates the level of similarity or identity of the sample to the reference, in the context of the proteins constituting the sample.

In some embodiments, the herein disclosed method is suitable for determining the presence of a mixture of proteins in the sample. In some embodiments, the herein disclosed method is suitable for determining the presence of a plurality of types of proteins in the sample. In some embodiments, the method is suitable for determining the presence or absence of pathogens that cause infection including viral and microbial infections, and in some embodiments, the method is suitable for determining the presence or absence of pathogens that do not cause diseases such as cancer, cardiovascular diseases and COPD.

In some embodiments, the proteins are derived from a subject. In some embodiments, the proteins are endogenous proteins derived from the subject. In some embodiments, the proteins are derived from a pathogen.

As used herein, the term "endogenous" refers to the proteins originating from the subject or a host (e.g., encoded from the genome of the subject or a host, produced by its cells, etc.).

In some embodiments, determining is by using a spectrometer.

In some embodiments, a spectrometer comprises an FTIR mass spectrometer.

Types of spectrometers, including methods of using same, are common and would be apparent to one of ordinary skill in the art of biochemistry and protein characterization. Non-limiting examples of such spectrometers, include but are not limited to, GS-MS, FTIR spectrometer, or others, such as exemplified herein.

In some embodiments, the inert gas is undetectable in mass spectrometry. In some embodiments, the inert gas is undetectable in FTIR mass spectrometry. In some embodiments, the inert gas comprises or consists of nitrogen ($N_2$). In some embodiments, the inert gas comprises or consists of helium ($H_2$). In some embodiments, the inert gas comprises or consists of a combination or a mixture of nitrogen and helium.

As used herein, the term "inert gas" encompasses any gas as long as it does not react with the air sample, including any portion thereof, e.g., a mixture of proteins, as described herein, and is undetectable in mass spectrometry, such as FTIR mass spectrometry.

In some embodiments, pumping is at a capacity of between about 0.5 liters/sec to about 10 liters/sec, about 1.5 liters/sec to about 12 liters/sec, about 2.0 liters/sec to about 11 liters/sec, about 5 liters/sec to about 10 liters/sec, or about 1.0 liters/sec to about 15 liters/sec. Each possibility represents a separate embodiment.

As used herein, "pumping" is by any means known to a person of skill in the art, such as, but not limited to a pump, a peristaltic pump, or others.

In some embodiments, a pressure higher or greater than the atmospheric pressure comprises a pressure of at least about 1.1 atmospheres (atm.), at least about 1.2 atm., at least about 1.3 atm., at least about 1.4 atm., at least about 1.5 atm., at least about 1.6 atm., at least about 1.7 atm., at least about 1.8 atm., at least about 1.9 atm., at least about 2.0 atm., at least about 2.1 atm., at least about 2.2 atm., at least about 2.3 atm., at least about 2.4 atm., at least about 2.5 atm., or at least about 3.0 atm., or any value and range therebetween. Each possibility represents a separate embodiment.

In some embodiments, a pressure higher or greater than the atmospheric pressure comprises a pressure of between about 1.1 atm. to about 2.5 atm, about 1.5 atm. to about 3.0 atm, about 1.4 atm. to about 2.3 atm, about 1.01 atm. to about 1.5 atm, about 1.05 atm. to about 1.45 atm. Each possibility represents a separate embodiment.

In some embodiments, a reference profile represents or is derived from a sample comprising a mixture of proteins. In some embodiments, a reference profile represents or is derived from a sample comprising a predetermined mixture of proteins. In some embodiments, a reference profile represents or is derived from a sample comprising a predetermined mixture of proteins, representing a known spectral pattern indicative of a physiological state, e.g., infected, non-infected, afflicted with a disease or a condition, healthy, normal, intact, or other. In some embodiments, the reference profile represents or is derived from a subject being positive to a pathogen.

In some embodiments, the reference profile represents or is derived from an exhaled air sample collected or obtained from a subject validated and/or confirmed to be afflicted with COVID-19, infected with or positive to SARS-COV-2, or any combination thereof.

In some embodiments, the method further comprises providing an air sample. In some embodiments, the method further comprises a step comprising obtaining or collecting an air sample. In some embodiments, the air sample comprises air exhaled from a subject. In some embodiments, the air sample comprises an environmental air. In some embodiments, the above disclosed step is preceding step (a) of the method described herein. In some embodiments, the above disclosed step is preceding the pumping as described herein.

As used herein, the term "environmental air" refers to air collected from or being derived from the environment. As used herein, the term "environmental air" refers to air not being collected from or derived directly from a subject (e.g., exhaled from a subject to a container as described herein).

In some embodiments, the subject is suspected of being infected with a pathogen. In some embodiments, the subject is a human subject.

In some embodiments, the pathogen is characterized by being capable of inducing an infectious disease. In some embodiments, the pathogen is characterized by being capable of inducing a respiratory infectious disease. In some embodiments, the pathogen is a virus. In some embodiments, the virus is a coronavirus.

Coronaviruses (CoVs) are the largest group of viruses belonging to the Nidovirales order, which includes Coronaviridae, Arteriviridae, and Roniviridae families. The Coronavirinae comprise one of two subfamilies in the Coronaviridae family, with the other being the Torovirinae. Coronaviruses are associated with illness from the common cold to more severe conditions such as Severe Acute Respiratory Syndrome (SARS-COV) and Middle East Respiratory Syndrome (MERS-COV). Severe acute respiratory syndrome coronavirus 2 (SARS-COV-2) is the positive-sense, single-stranded RNA coronavirus that causes the coronavirus disease 2019 (COVID-19), responsible for the 2019-20 Wuhan coronavirus outbreak. Coronaviruses are zoonotic, meaning they are transmitted between animals and people. Common signs of infection include respiratory symptoms, fever, coughing, shortness of breath and breathing difficulties. High concentrations of cytokines were recorded in plasma of critically ill patients infected with 2019-nCoV.

In some embodiments, the coronavirus comprises or is SARS-COV-2. In some embodiments, the subject is afflicted with COVID-19.

In some embodiments, the sample is prepared by using the system of the invention. In some embodiments, a spectral profile of the prepared sample is obtained by using the system of the invention. In some embodiments, the presence of a mixture of proteins in the prepared air sample is determined or detected by using the system of the invention.

Various examples of aspects of the presently disclosed subject matter are disclosed herein below.

According to one aspect of the presently disclosed subject matter there is provided a method of detecting infection of a subject by a pathogen, the method comprising: obtaining an exhaled air sample from a tested subject; analyzing the air sample using a spectroscopic device to thereby obtain a respective tested spectral profile, representing a spectral response of the air sample; comparing the tested spectral profile with at least one pathogen-specific profiles collection comprising a plurality of spectral profiles, each indicative of the presence of respective marker, out of a pathogen-specific collection of markers, in the air sample, and wherein the pathogen-specific collection of markers is indicative, when detected in a subject, of an infection of the subject with the specific pathogen; in case correlation between the tested spectral profile and the pathogen-specific profiles collection complies with at least one predefined condition, determining infection or suspected infection of the tested subject with the specific pathogen.

In some embodiments, the method further comprises a learning phase, comprising: analyzing exhaled air samples extracted from individuals positively tested to be infected by a certain pathogen, using a spectrometry device and generating a respective a first collection of markers; determining the pathogen-specific collection of markers based on the first collection of markets; determining, for each marker in the collection of markers a respective spectral-profile representing a spectral response of the maker obtained by a spectroscopic device; generating the pathogen-specific profiles collections that comprises the spectral profile of each marker in the collection of markers.

In some embodiments, the method further comprises condensing the exhaled air sample before analyzing using the spectroscopic device.

In some embodiments, determining a respective spectral-profile for each marker in the collection of markers, comprises: for each marker in the collection of markers: searching in libraries of the spectroscopic device a matching spectral profile.

In some embodiments, the method further comprises during the learning phase: obtaining a second collection of markers based on published literature; and determining the pathogen-specific collection of markers based on cross between the first collection of markets and the second collection of markers.

In some embodiments, the method further comprises: comparing the tested spectral profile with a plurality of different pathogen-specific profiles collections; wherein each collection comprises a plurality of spectral profiles, each spectral profile is indicative of the presence of respective marker, out of a pathogen specific collection of markers, in the air sample, and wherein the pathogen-specific collection of the markers is indicative, when detected in a subject, of an infection of the subject with the specific pathogen; in case correlation between the tested spectral profile and a given pathogen-specific profiles collection from the plurality of pathogen-specific profiles collections complies with at least one predefined condition, determining infection or suspected infection of the tested subject with the specific pathogen related to the given pathogen-specific profiles collection.

In some embodiments, the air sample comprises an exhaled volumetric organic compound (VOC).

In some embodiments, the spectroscopic device is a Fourier Transform InfraRed (FTIR) device. In some embodiments, the spectrometry device is a gas chromatography-mass spectrometry device.

In some embodiments, the pathogen-specific collection of markers comprises at least three different markers.

According to another aspect of the presently disclosed subject matter there is provided a system for detecting infection of a subject by a pathogen, the system comprising: a spectroscopic device and a processing circuitry; the spectroscopic device is configured to analyze an exhaled air sample, obtained from a tested subject, and generate a respective tested spectral profile, representing a spectral response of the air sample; the processing circuitry is configured to: compare the tested spectral profile with at least one pathogen-specific profiles collection comprising a plurality of spectral profiles, each indicative of the presence of respective marker, out of a pathogen-specific collection of markers, in the air sample, and wherein the pathogen-specific collection of markers is indicative, when detected in a subject, of an infection of the subject with the specific pathogen; and in case correlation between the tested spectral profile and the pathogen-specific profiles collection complies with at least one predefined condition, to determine infection or suspected infection of the tested subject with the specific pathogen.

In some embodiments, the system further comprises a condenser configured to condense the exhaled air sample and provide a condensed air sample to the spectroscopic device for testing.

In some embodiments, the spectroscopic device comprises or is otherwise operatively connected to a cooling chamber configured to receive the exhaled air sample during the analysis by the spectroscopic device; wherein the cooling chamber is configured to be cooled to sub-zero temperature allowing condensation of the exhaled air sample.

In some embodiments, the cooling chamber is configured to continuously receive a flow of a gaseous cooling agent in order to cool down and condense the exhaled air sample.

In some embodiments, the system further comprises a spectrometry device configured to analyze exhaled air samples extracted from individuals positively tested to be infected by a certain pathogen and generating a first collection of markers, wherein the pathogen-specific collection of markers is determined based on the first collection of markers; a processing circuitry configured to: determine, for each marker in the collection of markers a respective spectral-profile representing a spectral response of the maker obtained by a spectroscopic device; and generate the pathogen-specific profiles collections that comprises the spectral profile of each marker in the collection of markers.

According to another aspect of the presently disclosed subject matter there is provided a method of treating an infected individual with a specific pathogen, comprising:

obtaining an exhaled air sample from a tested subject; analyzing the air sample using a spectroscopic device, to thereby obtain a respective tested spectral profile, representing a spectral response of the air sample; comparing the tested spectral profile with at least one pathogen-specific profiles collection comprising a plurality of spectral profiles, each indicative of the presence of respective marker, out of a pathogen-specific collection of markers, in the air sample, and wherein the pathogen-specific collection of markers is indicative, when detected in a subject, of an infection of the subject with the specific pathogen; in case correlation between the tested spectral profile and the pathogen-specific profiles collection complies with at least one predefined condition, determining infection or suspected infection of the tested subject with the specific pathogen; providing to the tested subject treatment suitable for treating the specific pathogen.

In some examples the treatment includes providing a medication suitable for treating the specific pathogen.

In some examples the treatment includes administering public quarantining to the tested subject.

Wherein in some examples the method further comprising a learning phase, comprising: analyzing exhaled air samples extracted from individuals positively tested to be infected by a certain pathogen, using a spectrometry device and generating a respective a first collection of markers; determining the pathogen-specific collection of markers based on the first collection of markets; determining, for each marker in the collection of markers a respective spectral-profile representing a spectral response of the maker obtained by a spectroscopic device; generating the pathogen-specific profiles collections that comprises the spectral profile of each marker in the collection of markers.

According to another aspect of the presently disclosed subject matter there is provided a pathogen controlling system comprising: a corridor connected by one or more air ducts to a spectroscopic device; a processing circuitry; wherein the corridor is design to enable one or more subjects to pass through and is configured to: collect exhaled air from the one or more subjects passing through the corridor and deliver the air via the duct to the spectroscopic device; the spectroscopic device is configured to analyze an exhaled air sample, obtained from the subjects passing through the corridor, and generate a respective tested spectral profile, representing a spectral response of the air sample; the processing circuitry is configured to: compare the tested spectral profile with at least one pathogen-specific profiles collection comprising a plurality of spectral profiles, each indicative of the presence of respective marker, out of a pathogen-specific collection of markers, in the air sample, and wherein the pathogen-specific collection of markers is indicative, when detected in a subject, of an infection of the subject with the specific pathogen; and in case correlation between the tested spectral profile and the pathogen-specific profiles collection complies with at least one predefined condition, to determine infection or suspected infection of the one or more subjects passing though the corridor, with the specific pathogen.

According to another aspect of the presently disclosed subject matter there is provided a method of detecting infection of a subject by a pathogen, the method comprising: during a learning phase: analyzing exhaled air samples extracted from individuals positively tested to be infected by a certain pathogen, using a spectrometry device and generating a respective a first collection of markers; determining the pathogen-specific collection of markers based on the first collection of markets; determining, for each marker in the collection of markers a respective spectral-profile representing a spectral response of the maker obtained by a spectroscopic device; generating the pathogen-specific profiles collections that comprises the spectral profile of each marker in the collection of markers; during a testing phase: obtaining an exhaled air sample from a tested subject; analyzing the air sample using a spectroscopic device, to thereby obtain a respective tested spectral profile, representing a spectral response of the air sample; comparing the tested spectral profile with at least one pathogen-specific profiles collection comprising a plurality of spectral profiles, each indicative of the presence of respective marker, out of a pathogen-specific collection of markers, in the air sample, and wherein the pathogen-specific collection of markers is indicative, when detected in a subject, of an infection of the subject with the specific pathogen; in case correlation between the tested spectral profile and the pathogen-specific profiles collection complies with at least one predefined condition, determining infection or suspected infection of the tested subject with the specific pathogen.

In some embodiments, the presently disclosed subject matter further contemplates a non-transitory program storage device readable by a computer, tangibly embodying a program of instructions executable by the computer to perform various methods or parts thereof as disclosed herein. For example, instruction for executing a machine learning algorithm configured to determine correlation between different groups of spectral marker and respective pathogen infections and various characterizations of the infection is also disclosed.

Various features and advantages of the system and method described herein include one or more of the following:

1. The system and method are based on an ability to turn the exhaled breath sample into an aerosol with an average aero dynamic suspension time of droplets of more than about 1 minute, or more than about 2 minutes, or more than about 3 minutes, in an analyzer.
2. The system and method can be used in any mid IR spectrometry method based on detection in a gas cell with any optical length.
3. The system and method provides the ability to detect 5-20 times more organic compounds than any other Gas phase spectrometry analyzer by exploiting the dynamic equilibrium of the aerosol containing the organic compounds by virtue of the injector unit.
4. The system and method provides the ability to detect semi volatile compounds such as oleic acids, and non-volatile organic compounds such as proteins, utilizing any mid IR gas spectrometry method.
5. The injector unit is able to create an exhaled air/inert gas mixture that increases the aerodynamic suspension of aerosol droplets in the analyzer.
6. The injector unit creates motion of the air molecules that are being mixed with the inert gas.
7. The motion of the air molecules and the differences in humidity levels between the exhaled air sample and inert gas add additional energy gradients that may increase the aerodynamic suspension times of aerosol droplets.
8. The motion created between the two phases increases the probability of the IR beam to interact with organic compounds present in the exhaled air sample.
9. The testing chamber can be under pressure when the air mixture is yet to be injected, which may create an even spread of the droplets inside the test chamber thus increasing the amount of IR droplets interactions and thus the ability to detect more organic compounds.

General

As used herein the term "about" refers to +10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments unless the embodiment is inoperative without those elements.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

The invention claimed is:

1. A system comprising:

A pump configured to pump an air sample into a cooling chamber;

a cooling chamber configured to cool the exhaled air sample to a sub-zero temperature;

an inert gas source configured to provide inert gas at a pressure higher than atmospheric pressure;

an injector unit in fluid communication with the cooling chamber and the inert gas source, the injector unit configured to mix the cooled exhaled air and an inert gas provided from the inert gas source; and a testing chamber configured to analyze the mixed inert gas and cooled exhaled air, wherein the injector unit is configured to inject the mixed cooled exhaled air and inert gas mixture into the testing chamber at a high velocity to increase the aerodynamic length and the average droplet size in the cooled exhaled air and inert gas mixture.

2. The system of claim 1, further comprising a heating unit, wherein the heating unit comprises one or more heating elements configured to heat the test chamber to a temperature within the range of from about 30 to about 60° C.

3. The system of claim 2, wherein the heating unit comprises one or more heating elements configured to heat the inert gas prior to the provision of the inert gas to the injector unit.

4. The system according to claim 1, wherein the air sample is an exhaled air sample.

5. The system according to claim 1, wherein the pump delivers the air sample at a velocity of from about 0.5 liters/sec to about 10 liters/sec.

6. The system according to claim 1, wherein the inert gas is undetectable by a Fourier-transform infrared (FTIR) mass spectrometry.

7. The system according to claim 1, wherein the inert gas is provided to the injector unit at a pressure of between about 1.1 atm. to about 2.5 atm.

8. The system according to claim 1, further comprising a controller configured to control at least one or more of: the capacity of the pump, the temperature of the cooling chamber, the pressure of the inert gas provided by the inert gas source, and the power provided to the heating unit.

9. The system according to claim 1, further comprising a cooling unit configured to cool the air sample at a temperature of about −10 to about −30° C. for a period of from about 0.5 to about 5 minutes prior to being provided to the pump.

10. The system according to claim 1, further comprising a vacuum pump configured to provide a vacuum in the test chamber at a pressure of between about −30 to about −70 KPa.

11. A method for preparing an exhaled air sample for detection of a mixture of proteins in the exhaled air sample, the method comprising:

(a) pumping a sample comprising exhaled air from a container to a cooling chamber;

(b) cooling the sample from (a) to a subzero temperature in the cooling chamber;

(c) mixing in an injection unit the sample from (b) with an inert gas source at a pressure higher than the atmospheric pressure inside a test chamber;

(d) heating the mixed sample to a temperature ranging from about 30 to about 65° C.; and (e) injecting the sample from (d) into a test chamber at a high velocity to increase the aerodynamic length and the average droplet size in the sample from (d).

12. The method of claim 11, further comprising a step (f) comprising determining a spectral profile of the sample from (d), and comparing the spectral profile to a reference profile to determine the presence of one or more compounds of interest.

13. The method of claim 12, wherein determining the spectral profile is determined using a spectrometer selected from a mid-range IR spectrometer or an FTIR mass spectrometer.

14. The method of claim 11, wherein pumping the sample comprising exhaled air is carried out at a velocity of between about 0.5 liters/sec to about 10 liters/sec.

15. The method of claim 11, wherein injecting the sample from (d) is carried out a a pressure of between about 1.1 atmosphere to about 2.5 atmosphere.

16. The method of claim 12, wherein the referenced profile represents or is derived from a sample comprising said mixture of proteins.

17. The method of claim 11, wherein the air sample comprises air exhaled from a subject that is suspected of being infected with a pathogen.

18. The method of claim 11, further comprising cooling the air sample at a temperature of about −10 to about −30° C. for a period of from about 0.5 to about 5 minutes prior to (a).

19. The method of claim 11, wherein injecting the sample from (d) into a test chamber comprises injecting the sample at a velocity of from about 3 to about 15 liters per minute.

20. A system comprising:

a. an injector unit comprising a longitudinally-extending tubular housing having at least two inlets, and one outlet conduit, the outlet conduit containing an entry inlet, a mixed gas outlet, and being comprised of a curved tubular segment having its entry inlet positioned within the body of the injector unit, and its mixed gas outlet positioned outside the body of injector unit, wherein the entry inlet of the outlet conduit faces one of the at least two inlets; and b. an analyzer configured to detect compounds in an air sample and provide a spectral profile of the air sample, the analyzer being in fluid communication with the injector unit.

* * * * *